(12) United States Patent
Dai et al.

(10) Patent No.: US 10,539,506 B2
(45) Date of Patent: Jan. 21, 2020

(54) STRUCTURED ILLUMINATION MICROSCOPY IMAGING SYSTEM BASED ON LINE-SCANNING SPATIOTEMPORAL FOCUSING

(71) Applicant: Tsinghua University, Beijing (CN)

(72) Inventors: Qionghai Dai, Beijing (CN); Ziwei Li, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 102 days.

(21) Appl. No.: 15/790,714

(22) Filed: Oct. 23, 2017

(65) Prior Publication Data

US 2018/0328849 A1 Nov. 15, 2018

(30) Foreign Application Priority Data

May 15, 2017 (CN) .......................... 2017 1 0338155

(51) Int. Cl.
*G01N 21/64* (2006.01)
*G02B 21/06* (2006.01)
(Continued)

(52) U.S. Cl.
CPC ......... *G01N 21/6458* (2013.01); *G02B 21/06* (2013.01); *G02B 21/241* (2013.01); *G02B 21/361* (2013.01); *G02B 27/0068* (2013.01)

(58) Field of Classification Search
CPC .. G01N 21/6458; G02B 21/06; G02B 21/241; G02B 21/361; G02B 27/0068
See application file for complete search history.

(56) References Cited

U.S. PATENT DOCUMENTS

| 5,504,337 | A | * | 4/1996 | Lakowicz | .......... | G01N 15/1434 |
| | | | | | | 250/459.1 |
| 2004/0223156 | A1 | * | 11/2004 | McGrew | .............. | G02B 5/1809 |
| | | | | | | 356/364 |

(Continued)

FOREIGN PATENT DOCUMENTS

| CN | 103335988 A | 10/2013 |
| CN | 106441571 A | 2/2017 |

(Continued)

OTHER PUBLICATIONS

Chinese Office Action dated Dec. 18, 2018 for Chinese Application No. 201710338155.X.

*Primary Examiner* — Christine S. Kim
(74) *Attorney, Agent, or Firm* — David D. Brush; Westman, Chapmlin & Koehler, P.A.

(57) ABSTRACT

A microscopy imaging system is disclosed. The system includes: a femtosecond laser; an acousto-optic modulator, configured to periodically modulate an intensity of a laser light; a line-scanning component, configured to focus the laser light to form a line-shaped beam and to scan in a direction perpendicular to the line-shaped beam; a chromatic dispersion component, configured to generate spatial chirped laser pulses; a collimating lens, configured to converge components with different wavelengths dispersed by the chromatic dispersion component to propagate in parallel; a microscope component, configured to guide light passing through the collimating lens to illuminate the sample and capture a fluorescence image at a focal plane; and a synchronous control component, configured to synchronously control the acousto-optic modulator to modulate the intensity of the laser light, the line-scanning component to scan (Continued)

and the microscope component to capture fluorescence images, such that a reconstructed image is obtained according to the images.

10 Claims, 2 Drawing Sheets

(51) Int. Cl.
  *G02B 27/00* (2006.01)
  *G02B 21/36* (2006.01)
  *G02B 21/24* (2006.01)

(56) References Cited

U.S. PATENT DOCUMENTS

| | | | |
|---|---|---|---|
| 2012/0039567 A1* | 2/2012 | Herman | G02B 6/124 |
| | | | 385/37 |
| 2013/0181143 A1* | 7/2013 | Betzig | G02B 21/0032 |
| | | | 250/459.1 |
| 2015/0226950 A1* | 8/2015 | Booth | G01N 21/6456 |
| | | | 250/459.1 |
| 2016/0327776 A1* | 11/2016 | Tsia | G02B 21/0056 |
| 2018/0074304 A1* | 3/2018 | Hernandez-Cubero | |
| | | | G02B 21/0032 |

FOREIGN PATENT DOCUMENTS

| | | | |
|---|---|---|---|
| CN | 106547079 A | | 3/2017 |
| CN | 106645081 A | * | 5/2017 |
| CN | 106645081 A | | 5/2017 |

* cited by examiner

STRUCTURED ILLUMINATION MICROSCOPY IMAGING SYSTEM BASED ON LINE-SCANNING SPATIOTEMPORAL FOCUSING

TECHNICAL FIELD

The present disclosure relates to the field of computational photography, and more particularly, to a structured illumination microscopy imaging system based on line-scanning spatiotemporal focusing.

BACKGROUND

A two-photon fluorescence microscope images through nonlinear effects excited by a fluorescence light. The fluorescent light with a relative short wavelength may be produced by a laser light with a relative long wavelength, such that the two-photon fluorescence microscope has a deep penetration depth and few fluorescence excitations in defocus areas.

The conventional two-photon fluorescence microscope employs a point-scanning manner. However, a scanning speed based on the point-scanning manner decreases as a field of view increases. Therefore, it is hard to rapidly image a large field of view.

SUMMARY

Embodiments of the present disclosure provide a structured illumination microscopy imaging system based on line-scanning spatiotemporal focusing. The system includes: a femtosecond laser; an acousto-optic modulator, configured to periodically modulate an intensity of a laser light from the femtosecond laser; a line-scanning component, configured to focus the laser light modulated by the acousto-optic modulator to form a line-shaped beam and to scan in a direction perpendicular to the line-shaped beam; a chromatic dispersion component, configured to generate spatial chirped laser pulses; a collimating lens, configured to converge components with different wavelengths dispersed by the chromatic dispersion component to propagate in parallel; a microscope component, configured to guide light passing through the collimating lens to illuminate the sample and capture a fluorescence image at a focal plane; and a synchronous control component, configured to synchronously control the acousto-optic modulator to modulate the intensity of the laser light, the line-scanning component to scan and the microscope component to capture fluorescence images, such that a reconstructed image is obtained according to the images.

Additional aspects and advantages of embodiments of the present disclosure will be given in part in the following descriptions, become apparent in part from the following descriptions, or be learned from the practice of the embodiments of the present disclosure.

BRIEF DESCRIPTION OF THE DRAWINGS

The above and/or additional aspects and advantages of embodiments of the present disclosure will become apparent and more readily appreciated from the following descriptions made with reference to the drawings, in which.

DETAILED DESCRIPTION

Figure 1:
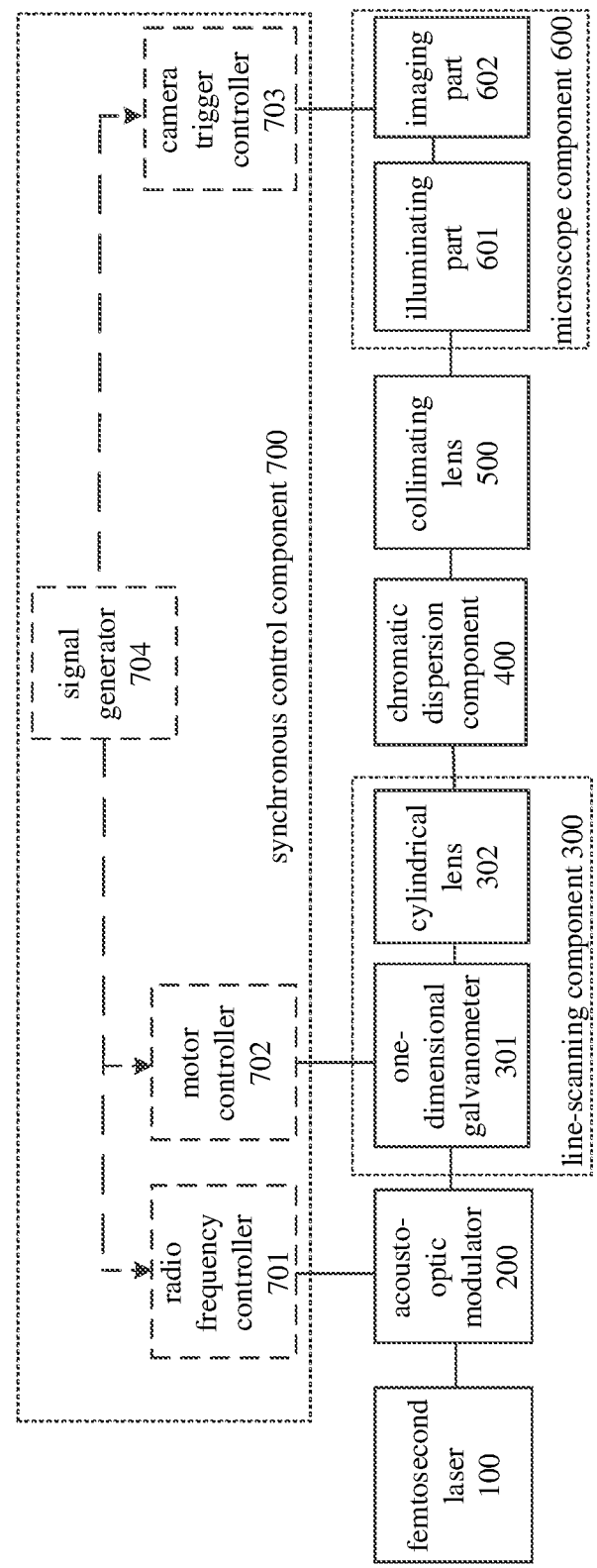
FIG. 1 is a schematic diagram illustrating a structured illumination microscopy imaging system based on line-scanning spatiotemporal focusing according to embodiments of the present disclosure.

Embodiments of the present disclosure will be described in detail and examples of embodiments are illustrated in the drawings. The same or similar elements and the elements having same or similar functions are denoted by like reference numerals throughout the descriptions. Embodiments described herein with reference to drawings are explanatory, serve to explain the present disclosure, and are not construed to limit embodiments of the present disclosure.

A structured illumination microscopy imaging system based on line-scanning spatiotemporal focusing provided by embodiments of the present disclosure will be described with reference to the drawings.

FIG. 1 is a schematic diagram illustrating a structured illumination microscopy imaging system based on line-scanning spatiotemporal focusing according to embodiments of the present disclosure.

As shown in FIG. 1, the system includes: a femtosecond laser 100, an acousto-optic modulator 200, a line-scanning component 300, a chromatic dispersion component 400, a collimating lens 500, a microscope component 600 and a synchronous control component 700.

The femtosecond laser 100 is configured to emit an ultrashort pulsed laser.

The acousto-optic modulator 200 is configured to modulate the intensity of the femtosecond laser light emitted by the femtosecond laser 100. In an embodiment, the acousto-optic modulator 200 is configured to modulate the intensity of the femtosecond laser light generated from the femtosecond laser 100 in a sinusoidal function. Attributed to the sinusoidal intensity modulation of the scanning laser, the system may generate structured illumination with sinusoidal stripes.

The line-scanning component 300 is configured to focus the laser light modulated by the acousto-optic modulator 200 to form a line-shaped beam, and to scan in a direction perpendicular to the line-shaped beams.

The chromatic dispersion component 400 is configured to generate spatial chirped laser pulses.

The collimating lens 500 is configured to converge components with different wavelengths dispersed by the chromatic dispersion component 400 to propagate in parallel.

The microscope component 600 is configured to guide light passing through the collimating lens to illuminate the sample and capture a fluorescence image at a focal plane.

The synchronous control component 700 is configured to output three channels of analog signal so as to synchronously control the acousto-optic modulator 200 to modulate the intensity of the laser light, the line-scan component 300 to scan and the microscope component 600 to capture fluorescence images, such that a reconstructed image is obtained according to the images.

With the system according to embodiments of the present disclosure, by illuminating through the line-scanning structured light whose intensity is modulated, in combination with a line-scanning spatiotemporal focusing manner, and by modulating the intensity of the laser light according to the sinusoidal function as well, the reconstructed image is obtained. Furthermore, a resolution and a contrast of the line-scanning spatiotemporal focusing manner are improved and excitation lights outside a focal plane due to scattering of objects are reduced.

That is to say, with the system according to embodiments of the present disclosure, by rapidly modulating the intensity of the light in periodicity via the acousto-optic modulator 200 in a sinusoidal function, only electronic control is adopted to obtain different phases and spatial frequencies, which has advantages of a rapid response, a flexible regulation and an easy operation.

Further, in an embodiment of the present disclosure, as shown in FIG. 1, the line-scanning component 300 includes: a one-dimensional scanning galvanometer 301 and a cylindrical lens 302.

The one-dimensional scanning galvanometer 301 is configured to rapidly scan in the direction perpendicular to the line-shaped beams. The cylindrical lens 302 is configured to focus light into the line-shaped beam. That is to say, the line-scanning component according to embodiments of the present disclosure may form the line-shaped beam via the cylindrical lens 302 and may rapidly scan in the direction perpendicular to the line-shaped beam via the one-dimensional scanning galvanometer 301.

Further, in an embodiment of the present disclosure, as shown in FIG. 1, the chromatic dispersion component 40 is configured to disperse a broadband light from the femtosecond laser light source via a blazed grating to widen a pulse width in the time domain. That is, the chromatic dispersion component 400 is configured to generate spatial chirped beams, for example, to disperse the broadband light via the blazed gating to widen the pulse width in the time domain.

Further, in an embodiment of the present disclosure, as shown in FIG. 1, the microscope component 600 includes: an illuminating part 601 and an imaging part 602.

The illuminating part 601 is configured to focus the chirped excitation light to illuminate the sample. The imaging part 602 is configured to capture a fluorescence image on the focal plane.

In detail, in an embodiment of the present disclosure, as shown in FIG. 1, the microscope component 600 guides the chirped excitation light into the illuminating part 601 via a dichroic mirror, and to capture the fluorescence image via the imaging part 602. The imaging part 602 includes a camera.

It may be understood that, in embodiments of the present disclosure, after the components with different frequencies are converged by the collimating lens 500 to propagate in parallel, when the microscopic component 600 is for example an epifluorescence microscope system, the chirped excitation light is guided into the illuminating path via the dichroic mirror. Furthermore, the components with different frequencies are of superposition with each other at the focal plane of an objective lens, thus having a shortest pulse width. The pulse width above or below the focal plane is rapidly widened, thus being unable to cause excitations. The imaging part captures the fluorescence image on the focal plane.

Further, in an embodiment of the present disclosure, as shown in FIG. 1, the synchronous control component 700 includes: a radio frequency controller 701, a motor controller 702, a camera trigger controller 703 and a signal generator 704.

The radio frequency controller 701 is connected to the acousto-optic modulator 200. The motor controller 702 is connected to the line-scanning component 300. The camera trigger controller 703 is connected to the microscope component 600. The signal generator 704 is connected to the radio frequency controller 701, the motor controller 702 and the camera trigger controller 703. The signal generator 704 is configured to synchronously control an output of the radio frequency controller 701, an output of the motor controller 702 and a camera trigger of the camera trigger controller 703.

Further, in an embodiment of the present disclosure, as shown in FIG. 1, the synchronous control component 700 is configured to repeatedly capture a plurality of images with different phases under a structured light with a given spatial frequency, and to obtain a reconstructed image by using a non-liner structural reconstruction algorithm.

Moreover, in an embodiment of the present disclosure, the synchronous control component 700 is configured to output three channels of analog signal via a data acquisition card.

It may be understood that, the synchronous control component 700 is configured to output the analog signal and the digital signal via the data acquisition card to synchronously control the intensity modulation, the galvanometer scanning and the camera capturing. Furthermore, the synchronous control component 700 is configured to capture a plurality of sets of images (such as 5 sets of images) with different phases under the structured light with the given spatial frequency, and to obtain a reconstructed image by using the non-liner structural reconstruction algorithm.

Further, in an embodiment of the present disclosure, the reconstruction image is obtained by a formula of:

$$I = \frac{I}{\sqrt{\Sigma_{m=1}^{4}(I_0-I_m)^2 + \Sigma_{m=2}^{4}(I_1-I_m)^2 + \Sigma_{m=3}^{4}(I_2-I_m)^2 + (I_3-I_4)^2}}$$

where, I denotes the intensity of the reconstructed image, $I_m$ denotes the intensity of an image captured under the lights with different phases, and m is a natural number for indicating different initial phases. For example, m equals to 0, 1 . . . 4, such that five numbers 0, 1 . . . 4 are configured to indicate five initial phases.

In an embodiment of the present disclosure, the different phases are 0°, 72°, 144°, 216° and 288°.

For example, as shown in FIG. 1, the system according to embodiments of the present disclosure includes: the femtosecond laser 100, the acousto-optic modulator 200, the line-scanning component 300 including the one-dimensional scanning galvanometer 301 and the cylindrical lens 302, the chromatic dispersion component 400, the collimating lens 500, the microscope component 600 including the illuminating part 601 and the imaging part 602, and the synchronous control component 700 including the signal generator 704 and controllers (the radio frequency controller 701, the motor controller 702 and the camera trigger controller 703). In detail, the femtosecond laser 100 includes an oscillator with a maximum power of 500 mW and a repeat frequency of 80 MHz, and has a center wavelength of 800 nm (which is the center wavelength of the wide wavelength range output from the femtosecond laser and is an important parameter of the femtosecond laser). The cylindrical lens 302 has a focal length $f_{cyl}=100$ mm. The collimating lens 500 has a focal length $f_{col}=200$ mm. The chromatic dispersion part 400 is a blazed grating with a linear destiny of 830 lines and a blazed wavelength of 800 nm. The microscope component 600 includes an objective lens, such as a water immersion objective of Olympus Cor. whose magnification is ×60 and NA (Numerical aperture)=1.0. The signal generator 704 is configured to generate 3 signals to synchronously control the output of the radio frequency controller 701, the output of the motor controller 702 and the camera trigger of the camera trigger controller 703, to correspondingly control the acousto-optic modulator 200, the one-dimensional galvanometer 301 and the camera respectively.

Figure 2:
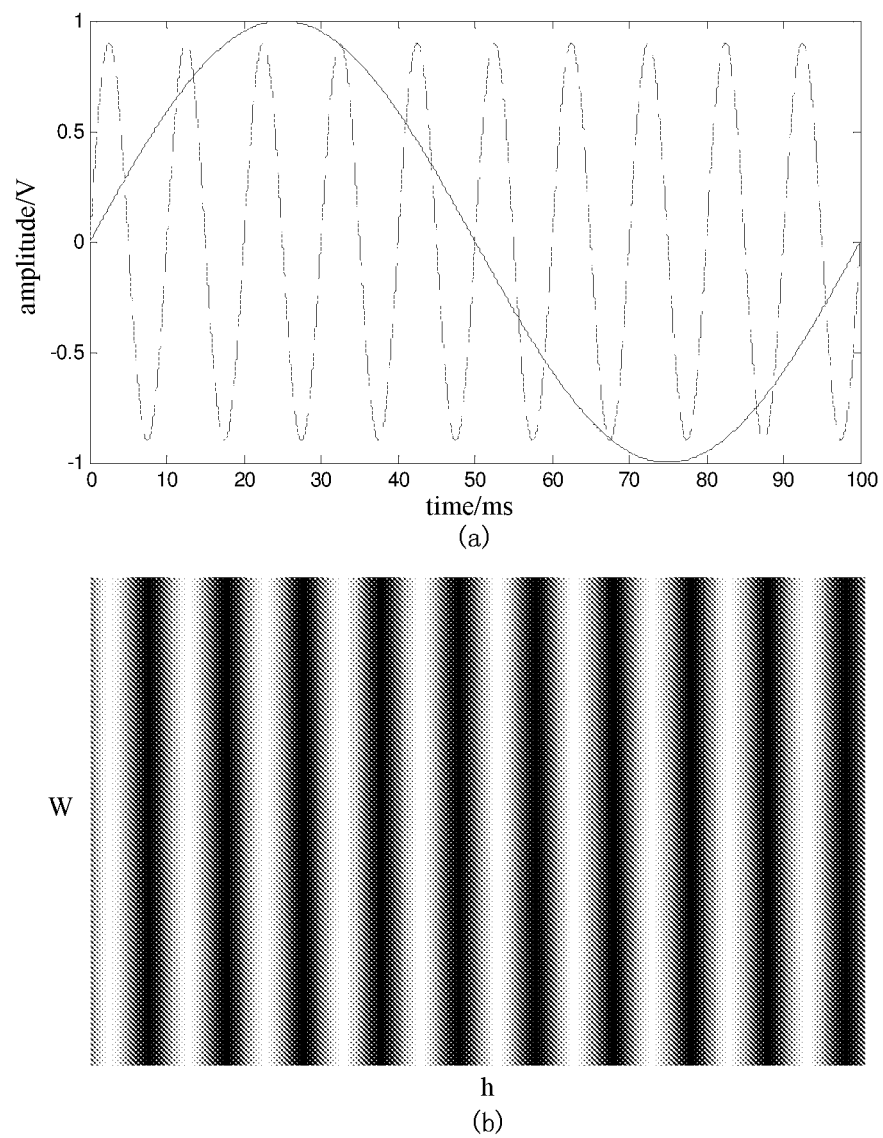
FIG. 2 is a diagram illustrating an intensity modulation signal and a sinusoidal structured light generated within a scanning period.

Within each scanning cycle, the one-dimensional scanning galvanometer 301 scans once in the scanning direction perpendicular to the line-shaped beams. Supposes that the scanning period is $T_{gal}$, if a scanning angle range is about $\theta=\pm2°$, a scanning angle speed is correspondingly $\omega_{gal}=\theta/T_{gal}$. Taking a flat field approximation into consideration when the scan angle is small, a moving speed of line-shaped beams on the surface of the grating is $v_{beam}=\omega_{gal}*f_{cyl}=\theta*f_{cyl}/T_{gal}$, where $f_{cyl}$ is the focal length of the cylindrical lens 302. Supposed that the number of cycles of the sinusoidal stripes scanned once is S, the frequency of a sinusoidal modulation signal of the acousto-optic modulator 200 is $f_{aom}=1/(T_{gal}/S)=S/T_{gal}$, the spatial frequency of the sinusoidal stripes is correspondingly $f_s=S/h$, where h denotes a width of a field of view in the scanning direction. In theory, $f_s$ may take a maximum value that is equal to a cut-off frequency $f_0$ of the system. In order to ensure that components with all frequencies may pass through an aperture behind the objective lens, the value of $f_s$ may be smaller than that of $f_0$. In practice, performances of different spatial frequencies may be texted by using the frequency of the radio frequency control signal for regulating the acousto-optic modulator 200. As shown in FIG. 2, a case that $T_{gal}=0.1$ s, S=10 and the initial phase of the acousto-optic modulator is 0°, a schematic diagram of a scanning result and a control signal for modulating the acousto-optic modulator is shown as FIG. 2(a); and the corresponding structured light is shown in FIG. 3(b).

For a non-line imaging manner of Dual-photon, it is required to collect five sets of images, the five sets of images each having phases spaced by an interval of 72° with each other to reconstruct a same sample plane. Varieties of the phases may be done precisely by easily regulating the initial phase of the radio frequency control signal of the acousto-optic modulator. A high-resolution image is reconstructed with five phase-shifted images (the phases are 0°, 72°, 144°, 216° and 288°) by a formula of:

$$I=\sqrt{\Sigma_{m=1}^{4}(I_0-I_m)^2+\Sigma_{m=2}^{4}(I_1-I_m)^2+\Sigma_{m=3}^{4}(I_2-I_m)^2+(I_3-I_4)^2}.$$

It is to be illustrated that, in addition to an acquisition of information about higher spatial frequencies, embodiments of the present disclosure may also filter background noise that is not modulated. Therefore, the contrast of the image captured by the structured light microscopic imaging system is further improved.

The structured illumination microscope employs a computational microscopy technology whose collection capacity is improved by illuminating via the structured light of sinusoidal stripes with different phases. By shifting the phases, spatial frequencies beyond the cut-off frequency of the system may be collected. With the structured illumination technology, it is solved that the resolution and the contrast of the line-scanning spatiotemporal focusing manner become low when an object with a high scattering coefficient is imaged. On the basis of the line-scanning structured light whose intensity is modulated, the resolution of the system is improved. By filtering a DC component of the background noise, the contrast is improved.

In detail, in the structured illumination microscopy technology of two-photon imaging system based on Line-Scanning Temporal Focusing Microscopy (LSTFM for short), the spatiotemporal focusing (TF for short) technology is a two-photon microscopy technology based on compressing in the time domain. Moreover, the spatiotemporal focusing (TF) technology may realize a tomography on the basis of a flat illumination manner and have a high imaging speed. However, the spatiotemporal focusing (TF) technology has a lower resolution and is more susceptible to the scattering of samples, compared with the two-photon microscope based on a point-scanning manner. As a result, the spatiotemporal focusing (TF) technology is greatly limited in applications of the field of bioscience. In embodiments of the present disclosure, the cylindrical lens 302 is introduced into the LSTFM on the basis of the TF technology which is used for flat imaging. By capturing a two-dimensional image with the one-dimensional line-scanning manner, the resolution and the robustness of scattering are improved on the basis of the high imaging speed. In order to further improve the resolution and further reduce the excitation lights outside the focal plane, embodiments of the present disclosure introduce a structured light for illuminating, in combination with the line-scanning manner of the LSTFM, the intensity of the excitation light is modulated according to the sinusoidal function in the time dimension. By synchronous controlling the scanning and the intensity modulation, the structured light of sinusoidal stripes for illuminating is obtained. An intensity of the excitation light is modulated rapidly by the acousto-optic modulator.

With the system based on line-scanning spatiotemporal focusing, by introducing the acousto-optic modulator into a light path which is line-scanned and spatiotemporal focused, by synchronous controlling the intensity modulation and the scanning, and by introducing the structured light for illuminating in the spatiotemporal focusing technology, the resolution and the contrast of imaging a biological sample with a capacity of scattering is improved. The structured light is generated dependent on the intensity modulation synchronously varied with line-scanning. With the line-scanning structured light whose intensity is modulated for illuminating, and in cooperation with the line-scanning spatiotemporal focusing manner, and the synchronous modulation of the intensity of the excitation light according to the sinusoidal function, the reconstructed image is obtained. Furthermore, the resolution and the contrast of the line-scanning spatiotemporal technology are improved and the excitation light outside the focal plane caused by the scattering are reduced. Compared with the conventional grating interferometry, the sinusoidal structured light is generated more rapidly and it is easier to regulate phases and frequencies. With the structured light technology, the resolution and the contrast of the lint-scanning spatiotemporal technology are improved and it is more robust to the scattering of the objects.

In the specification, it is to be understood that, relative terms such as "central", "longitudinal", "lateral", "length", "width", "height", "above", "below", "left", "right", "front", "rear", "vertical", "horizontal", "top", "bottom", "inner", "outer", "clockwise", "anticlockwise", "axial", "radial", "circumference direction", as well as derivative thereof construed to refer to the orientation as then described or as shown in the drawings under discussion for simplifying the description of the present disclosure, but do not alone indicate or imply that the device or element referred to must have a particular orientation. Moreover, it is not required that the present disclosure is constructed or operated in a particular orientation and therefore are not construed to limit embodiments of the present disclosure.

In the description of the present disclosure, "a plurality of" means at least two, for example, two, three or more, unless specified otherwise.

In the description of the present disclosure, unless specified or limited otherwise, the terms "mounted," "connected," "coupled" and "fixed" and variations thereof are used broadly and encompass such as fixed, removable mountings, connections and couplings, or may be integral; also may be mechanical or electrical mountings, connections and couplings; also can be direct or indirect mountings, connections and couplings, or further may be inner mountings, connections and couplings or interaction relation of two components, which can be understood by those skilled in the art according to the detail embodiment of the present disclosure.

In the description of the present disclosure, reference throughout this specification to "an embodiment," "some embodiments," "example," "a specific example," or "some examples," means that a particular feature, structure, material, or characteristic described in connection with the embodiment or example is included in at least one embodiment or example of the present disclosure. In the specification, the terms mentioned above are not necessarily referring to the same embodiment or example of the present disclosure. Furthermore, the particular features, structures, materials, or characteristics may be combined in any suitable manner in one or more embodiments or examples. Besides, any different embodiments and examples and any different characteristics of embodiments and examples may be combined by those skilled in the art without contradiction.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A structured illumination microscopy imaging system based on line-scanning spatiotemporal focusing, comprising:
    a femtosecond laser;
    an acousto-optic modulator, configured to periodically modulate an intensity of a laser light from the femtosecond laser;
    a line-scanning component, configured to focus the laser light modulated by the acousto-optic modulator to form a line-shaped beam and to scan in a direction perpendicular to the line-shaped beam;
    a chromatic dispersion component, configured to generate spatial chirped laser pulses wherein the chromatic dispersion component comprises a blazed grating, and the blazed grating is configured to disperse the line-shaped beam with broadband to widen a pulse-width in time domain;
    a collimating lens, configured to converge components with different wavelengths dispersed by the chromatic dispersion component to propagate in parallel;
    a microscope component, configured to guide light passing through the collimating lens to illuminate the sample and capture a fluorescence image at a focal plane; and
    a synchronous control component, configured to synchronously control the acousto-optic modulator to modulate the intensity of the laser light, the line-scanning component to scan and the microscope component to capture fluorescence images, such that a reconstructed image is obtained according to the images.

2. The system according to claim 1, wherein the acousto-optic modulator is configured to periodically modulate the intensity of the laser light from the femtosecond laser according to a sinusoidal function.

3. The system according to claim 1, wherein the line-scanning component comprises:
    a one-dimensional scanning galvanometer, configured to scan rapidly in the direction perpendicular to the line-shaped beams; and
    a cylindrical lens, configured to focus light into the line-shaped beam.

4. The system according to claim 1, wherein the microscope component comprises:
    an illuminating part, configured to focus the chirped excitation light to illuminate the sample; and
    an imaging part, configured to capture a fluorescence image on the focal plane.

5. The system according to claim 4, wherein the microscope component is configured to guide the chirped excitation light into the illuminating part through a dichroic mirror, and to capture the fluorescence image via the imaging part.

6. The system according to claim 1, wherein the synchronous control component comprises:
    a radio frequency controller, connected to the acousto-optic modulator;
    a motor controller, connected to the line-scanning component;
    a camera trigger controller, connected to the microscope component; and
    a signal generator, connected to the radio frequency controller, the motor controller and the camera trigger controller, and configured to synchronously control an output of the radio frequency controller, an output of the motor controller and a camera trigger of the camera trigger controller.

7. The system according to claim 6, wherein the different phases comprises 0°, 72°, 144°, 216° and 288°.

8. The system according to claim 1, wherein the synchronous control component is configured to capture a plurality of images with different phases under a structured light with a given spatial frequency, and to obtain a reconstructed image by using a non-liner structural reconstruction algorithm.

9. The system according to claim 8, wherein the reconstructed image is obtained by a formula of:

$$I = \sqrt{\Sigma_{m=1}^{4}(I_0 - I_m)^2 + \Sigma_{m=2}^{4}(I_1 - I_m)^2 + \Sigma_{m=3}^{4}(I_2 - I_m)^2 + (I_3 - I_4)^2}$$

where, I denotes an intensity of the reconstructed image, $I_m$ denotes an intensity of an image captured under lights with different phases, and m is a natural number for indicating different initial phases.

10. The system according to claim 1, wherein the synchronous control component is configured to output three channels of analog signal to control the acousto-optic modulator, the line-scan component and the microscope component via a data acquisition card.

* * * * *